(12) United States Patent
Aue

(10) Patent No.: US 10,729,413 B2
(45) Date of Patent: Aug. 4, 2020

(54) MEDICAL INSTRUMENT FOR ENDOSCOPIC SURGERY

(71) Applicant: OLYMPUS WINTER & IBE GMBH, Hamburg (DE)

(72) Inventor: Thomas Aue, Wedel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 548 days.

(21) Appl. No.: 15/326,878

(22) PCT Filed: Aug. 5, 2015

(86) PCT No.: PCT/EP2015/001611
§ 371 (c)(1),
(2) Date: Jan. 17, 2017

(87) PCT Pub. No.: WO2016/023624
PCT Pub. Date: Feb. 18, 2016

(65) Prior Publication Data
US 2017/0202547 A1    Jul. 20, 2017

(30) Foreign Application Priority Data
Aug. 15, 2014 (DE) ......................... 10 2014 012 036

(51) Int. Cl.
*A61B 18/14* (2006.01)
*A61B 17/00* (2006.01)
(Continued)

(52) U.S. Cl.
CPC .... *A61B 17/00234* (2013.01); *A61B 17/2909* (2013.01); *A61B 18/1442* (2013.01);
(Continued)

(58) Field of Classification Search
CPC .......... A61B 17/00234; A61B 17/2909; A61B 2017/0042; A61B 2017/0046;
(Continued)

(56) References Cited

U.S. PATENT DOCUMENTS 5,741,286 A    4/1998  Recuset
6,245,085 B1 *  6/2001  Benecke ................ A61B 17/29
                                                                   606/174

(Continued)

FOREIGN PATENT DOCUMENTS

CN    103189780 A    7/2013
DE    19853305 C1   10/2000
(Continued)

OTHER PUBLICATIONS

Feb. 21, 2017 International Preliminary Report on Patentability issued in International Patent Application No. PCT/EP2015/001611.
(Continued)

*Primary Examiner* — Michael F Peffley
(74) *Attorney, Agent, or Firm* — Oliff PLC

(57) ABSTRACT

A medical instrument for endoscopic surgery, including a sheath tube having a distal and a proximal end and a connecting body arranged at the sheath tube's proximal end area, whereby the sheath tube and connecting body are penetrated in axial direction by a common channel, through which an elongated actuating element passes, an end body connectable to connecting body having a hand grip attached for operating the medical instrument, a locking slider, which is slidably housed in a channel oriented at an angle to the channel within connecting body, whereby the actuation area of locking slider projects from connecting body and can be actuated to locked and free positions using finger pressure, such that the end body coupled to connecting body is positively locked to connecting body in the locked position,
(Continued)

and the end body in the free position can be detached from connecting body.

9 Claims, 3 Drawing Sheets

(51) Int. Cl.
    *A61B 17/29*     (2006.01)
    *A61B 90/00*     (2016.01)

(52) U.S. Cl.
    CPC ............... *A61B 2017/0042* (2013.01); *A61B 2017/0046* (2013.01); *A61B 2017/00477* (2013.01); *A61B 2017/293* (2013.01); *A61B 2090/0813* (2016.02)

(58) Field of Classification Search
    CPC .... A61B 2017/00477; A61B 2017/293; A61B 18/1442
    See application file for complete search history.

(56) References Cited

U.S. PATENT DOCUMENTS

| | | | | |
|---|---|---|---|---|
| 6,423,054 | B1* | 7/2002 | Ouchi | A61B 10/06 600/117 |
| 2002/0082640 | A1* | 6/2002 | Scholer | A61B 17/29 606/205 |
| 2008/0046002 | A1 | 2/2008 | Renger et al. | |
| 2008/0109005 | A1* | 5/2008 | Trudeau | A61F 2/4425 606/99 |
| 2008/0157488 | A1* | 7/2008 | Kullmer | A61B 17/00 279/76 |
| 2008/0208246 | A1 | 8/2008 | Livneh | |
| 2011/0306952 | A1* | 12/2011 | Chen | A61B 17/29 606/1 |
| 2012/0271347 | A1* | 10/2012 | Kaercher | A61B 17/29 606/205 |
| 2013/0267782 | A1 | 10/2013 | Wieters et al. | |
| 2016/0206337 | A1 | 7/2016 | Karcher et al. | |

FOREIGN PATENT DOCUMENTS

| | | |
|---|---|---|
| DE | 10038085 A1 | 3/2001 |
| DE | 10064623 C1 | 8/2002 |
| DE | 102006038517 A1 | 2/2008 |
| DE | 102006062421 A1 | 7/2008 |
| DE | 102011007121 A1 | 10/2012 |
| EP | 1889578 A3 | 12/2008 |

OTHER PUBLICATIONS

Sep. 22, 2015 International Search Report issued in International Patent Application No. PCT/EP2015/001611.

* cited by examiner

MEDICAL INSTRUMENT FOR ENDOSCOPIC SURGERY

BACKGROUND OF THE INVENTION

The invention relates to a medical instrument for endoscopic surgery.

Instruments for endoscopic surgery generally include a sheath tube with a connecting body arranged at the proximal end area of the sheath tube, a push/pull rod leading through the sheath tube with an end effector attached to the distal end area of the rod, and a hand grip attachable to the rod for the guiding of instruments and for actuating the end effector. For cleaning purposes and for the ability to adapt to different applications, such instruments are traditionally designed to be disassembled.

For creating a detachable connection between the hand grip and the sheath tube, the hand grip is traditionally attachable to the connecting body via a coupler. The connecting body also serves as a rotary handle for rotating an end effector arranged at the distal end of the rod. For this purpose, the rod is typically non-rotatably connectable to the sheath tube. In such embodiments, the proximal end of the rod leading through the sheath tube can be connected with the hand grip in a positive lock.

An important aspect in the design of the aforementioned type of instruments intended for disassembly is the mechanism for creating a coupling connection between the individual parts. Traditionally, the coupling mechanisms are designed in such a way that the disengagement of at least two parts is carried out by overcoming a spring-loaded locking mechanism. For doing so, a locking slider spring-mounted in a transverse shaft in the connecting body can be actuated using finger pressure. In designing the locking slider, special attention is paid to enabling quick and easy operation on the one hand, and guaranteeing a high degree of reliability against malfunctions on the other. Moreover, the compact integration of the locking slider into the connecting body is desirable for the production of slender, lightweight instruments.

A generic instrument is known from DE 100 64 623 C1, which is constructed from a plurality of parts intended for disassembly. According to this prior art, it can be provided that a locking slider is housed in a shaft of a connecting body and held in place by spring force. For this purpose, it is proposed to arrange a coil spring outside of the connecting body in a direction coaxial to the locking slider, whereby a first end of the coil spring is supported by the periphery of the shaft opening in a wall of the connecting body, and the second end of the coil spring presses against a radial projection of the locking slider.

This manner of construction, having an exposed spring on the exterior of the medical instrument, has proved to be disadvantageous for a variety of reasons. One aspect is the difficulty of cleaning of such instruments. The spring elements arranged on the exterior of the device form a variety of edges and crevices, making it quite cumbersome to clean away germs and residue associated with substances coming into contact with the instrument. Moreover, the hazard exists of body tissue or other material passing by the spring element, for example sutures for the closing of open wounds or incisions, becoming caught on the edges of the spring element. This can lead to the holding mechanism becoming jammed or to difficulties in using the instrument.

BRIEF SUMMARY OF THE INVENTION

It is the object of the present invention to provide a medical instrument of the aforementioned type, which features good usability and ease of cleaning while also offering improved protection against malfunctions.

This problem will be solved by an object having the features of a medical instrument for endoscopic surgery, comprising a sheath tube having a distal and a proximal end and a connecting body arranged at the proximal end area of the sheath tube, whereby the sheath tube and the connecting body are penetrated in the axial direction by a common channel, through which an elongated actuating element passes, an end body connectable to the connecting body having a hand grip attached for operating the medical instrument, a locking slider, which is slidably housed in a channel oriented at an angle to the channel within the connecting body, whereby the actuation area of the locking slider projects from the connecting body and can be actuated to locked and free positions using finger pressure, such that the end body coupled to the connecting body is positively locked to the connecting body in the locked position, and the end body in the free position can be detached from the connecting body, and whereby the locking slider is held in the locked position by the tension of a spring element, characterized in that the spring element is arranged in the channel between the actuation area and the channel.

The device according to the invention is a medical instrument for endoscopic surgery, comprising a sheath tube having a distal and a proximal end and a connecting body arranged at the proximal end area of the sheath tube, whereby the sheath tube and the connecting body are penetrated in the axial direction by a common channel, through which an elongated actuating element passes, an end body connectable to the connecting body having a hand grip attached for operating the medical instrument, a locking slider, which is slidably housed in a shaft oriented at an angle to the channel within the connecting body, whereby the actuation area of the locking slider projects from the connecting body and can be actuated to locked and free positions using finger pressure, such that the end body coupled to the connecting body is positively locked to the connecting body in the locked position, and the end body in the free position can be detached from the connecting body, and whereby the locking slider is held in the locked position by spring tension, and whereby it is provided according to the invention that the spring element is arranged in the shaft between the actuation area and the channel.

If the spring element is arranged beneath the canal, then layers of relatively strong material have to be provided in the surrounding wall areas, which results in the connecting body being generally wider and heavy, thus leading to difficulties in handling the instrument. A design of this sort is known from DE 10 2006 038 517 A1. Typically, placing the spring element, for example in the form of a coil spring, beneath the locking slider, namely makes it necessary to incorporate a flat supporting surface into the interior wall of the connecting body. Given the rounded exterior geometry of the connecting body, correspondingly thick walls will be required. In addition, an empty volume must be provided beneath the locking slider large enough to accept the spring element and to allow the spring to travel.

Placing the spring element between the actuating area of the locking slider and particularly axial to the canal running through the connecting body makes it possible to take maximum advantage of the space within the connecting body. In this embodiment, only a small amount of empty volume is necessary in the shaft beneath the locking slider, namely just enough to allow a path along which the locking slider can slide. Full advantage can be taken of the space beneath the locking slider as it slides along its path.

In principle, it is conceived that the locking slider shaft will run at an angle to the channel, in particular meaning oblique to the longitudinal axis of the connecting body. This simplifies the design of the locking mechanism for locking the end body that supports the hand grip. In particular, on the locking slider a hook can be arranged, which is positively guided to move along with the locking slider and, for locking, to engage with an annular ring in the end body. It is preferentially conceived that the shaft in which the locking slider is housed be designed to lead in a direction transverse to the longitudinal axis of the sheath tube.

For providing good locking mechanism usability, it is provided that the actuating area of the locking slider will project from an opening in the connecting body. Preferably, the actuating area will be designed to be integral with the locking slider. Alternatively, it is conceivable that the actuating area be removably attached to the locking slider.

In a preferential embodiment of the invention, it is conceived that the spring element will be supported at a first end by a support surface situated in the channel area facing along the spring away from the actuating area, and supported at a second end by a contact surface on the locking slider facing along the spring toward the actuating area.

Depending on the type of spring element, it is conceivable that the spring element will be supported via support elements such as washers, bars or the like on the locking slider contact surface beneath the actuating area and/or on the support surface in the channel area. The contact surface can, for example, be a recessed annular groove on the shaft wall. Similarly, the contact surface may be an annular groove around the circumference of the locking slider. Alternatively, the support surface can be provided on a separately executed component of the connecting body. For example, the support surface can be provided on an insertable sleeve on the connecting body. This manner of component can, for example, be a guide element for guiding the detachable end body onto the connecting body. Regarding a sleeve-like component, it is conceivable that the axial sleeve passage will comprise the channel for the actuating element. In doing so, the support surface is provided on an outer wall of the sleeve. The sleeve-like component with the support surface can also be designed for conducting voltage to an electrical connection in the instrument. For this purpose, the component can, for example, be manufactured from an electrically conductive material.

In one advantageous embodiment, it is conceived that the spring element will be arranged in an interstice in the locking slider. Preferably, the interstice will be a tunnel-like break in the locking slider, specifically transverse to the direction of the shaft. Especially advantageous is incorporating the interstice into the locking slider in a direction transverse to the channel. The interstice can be bordered in a direction axial to the connecting body, thus distal and proximal to the wall surfaces of the locking slider.

Integrating the spring element into an interstice in the locking slider offers two immediate advantages. On the one hand, the above-mentioned disadvantages of difficulty in cleaning, or rather the development of additional edges and crevices on the exterior of the connecting body will be avoided, and, on the other hand, maximum advantage will be taken of the space inside the connecting body.

Given a special variant of medical instrument, it is provided that a junction will be arranged on the end body for an electrical power coupling in the sheath tube and/or in an actuating element leading through the sheath tube. As mentioned, the actuating element can be a push/pull rod leading through the channel.

In terms of electric voltage, the high-frequency output from a high-frequency generator and/or either a DC or a common AC voltage source can be provided. Furthermore, it can be provided that the medical instrument be of monopolar or bipolar design. This means that one or two electrical contacts for electric voltage output can be provided at the junction, which is preferably of plug-in design.

Regarding an end body in engagement with the connecting body, it is conceived that at least one electric voltage will be transmitted via an electrically conductive path in the end body to at least one electrically conductive component within the connecting body. It is further conceived that an electric voltage will be transmitted via the electrically conductive component within the connecting body in the area of the locking slider shaft to an electrically conducting path in the sheath tube. The electric voltage can be transmitted via the electrically conducting path in the sheath tube to an end effector arranged at the distal end area of the sheath tube. It is additionally conceived that the electrically conducting component will comprise the support surface for supporting the spring according to the invention. This can reduce the number of instrument components or the complexity of the instrument components.

In one preferential embodiment of the instrument, it is provided that the locking slider comprises an opening through which the actuating element passes. Preferably, the spring element is arranged above the opening. The arrangement of the spring element above the opening and below the actuation area of the locking slider results in an improved use of the space inside the locking slider shaft, or rather inside the connecting body.

Preferably, the locking slider opening has an inner contour, due to which the actuating element leading through the sheath tube and through the connecting body can be prevented from rotating. For this purpose, it is conceived that the opening will comprise a passage zone and a holding zone, whereby, in the free position, the locking slider allows a proximal section of the actuating element leading through the channel to freely pass through the passage zone, and, in the locked position, an engagement zone of the actuating element encompasses and positively locks free of rotation with the holding zone. Details of the rotation-free connection may be carried out, for example, as per the DE 100 64 623 C1 publication, to which explicit reference is hereby made.

In a particularly preferential structural embodiment of the instrument, it is provided that the spring element is of a coil spring design. It is further preferential that the cross-sectional area of the spring element in the form of a coil spring will taper from the first end to the second end. It is in particular conceived that a conical spring, in particular a conical compression spring, will be used. Particularly given a radially symmetrical design of the spring element, it is conceived that the spring element be arranged in the shaft in a direction coaxial to the locking slider.

The coil spring having a conical design simplifies the structural development of the locking slider. The tapered end of the coil spring, which is in particular designed to be narrower than the cross-section of the locking slider, can for this purpose easily be supported on a contact surface beneath the locking slider area of actuation. The wide end of the coil spring, which in particular projects laterally beyond the cross-section of the locking slider, can for this purpose be supported on a support surface in the area of the channel. Means of support at the lower end and/or at the upper end of the spring such as thrust washers, bars or the like, can be omitted in this embodiment. This reduces the complexity of the component and reduces the likelihood that the coupling mechanism will fail.

As explained, regarding the use of monopolar or bipolar instruments, it can be provided that an electric voltage is transmitted to the instrument sheath tube via a component within the connecting body developed for this purpose. As mentioned, the support surface for supporting the spring element within the connecting body can be arranged on the electrically conductive component. In a simple embodiment, the component made of an electrically conductive solid material may consist of a metal such as stainless steel or the like. If the spring element likewise consists of an electrically conductive material such as stainless steel, the spring being supported by the component will also be charged with electric voltage.

Regarding such structures, compliance with standards related to the safety of electrical instruments is to be taken into consideration. Since the upper end of the coil spring ends directly below the actuation area of the locking slider, the distance will be reduced between an electrically conductive point within the connecting body, in particular within the locking slider shaft, and the exterior of the connecting body. Given this structure, the hazard may exist of the electric voltage being transmitted or flashing over to part of the body of the person operating the medical instrument. This risk exists in particular while operating the locking slider by applying finger pressure to the actuating area.

The electric signal can in particular be conducted to part of the operator's body through a gap between the locking slider and the interior wall of the locking slider shaft. This danger is heightened when, for example, liquids or moisture penetrate into the gap between the locking slider and the interior wall of the locking slider shaft.

By means of designing the structure of the coil spring as a tapering or conical compression spring, the hazard of electric voltage being transmitted to the operator will be reduced. For this purpose, it is conceived that the upper end supported on a locking slider contact surface beneath the actuating area will be tapered with respect to the end supported on a support surface in the channel area.

A coil spring of conical design improves the operational safety of the instrument from both a mechanical as well as an electrical viewpoint.

In a preferred embodiment, it can be provided that, at least in the section provided for the spring element between the actuating area and the channel, the locking slider will comprise a cross-section which is narrower in a first direction and wider in a second direction than a cross section at the first end of the spring element. In this regard, it can also be provided that, at least in the section of the locking slider provided for this purpose, the spring element at its first end will project above at least portions of the locking slider cross-section.

It is preferentially conceived that the locking slider will have a substantially rectangular cross-section. It is particularly preferential that the cross-sectional shape of the locking slider be longer in a direction axial to the sheath tube than in a direction transverse to the sheath tube. The locking slider cross-section is therefore preferably elongated in shape, whereby the locking slider in its operating position within the shaft is preferably arranged with its long side transverse to the longitudinal length of the connecting body. Doing so has structural advantages for locking the actuating element at the axially-oriented locking slider opening.

It can be provided according to the invention that a conically shaped coil spring can be inserted laterally into the interstice in the locking slider. It is in particular provided that the coil spring be surrounded by the surfaces of two opposite walls of the locking slider defining the interstice, and at least the first, lower end of the coil spring between the opposite walls of the locking slider projects beyond the edge of the interstice. By doing so, the spring portions projecting past the edge of the interstice can be supported against a component mounted in place onto the locking slider. This component may—as mentioned—be an electrically conductive component. The support surface in contact with the spring can be charged with an electric signal or an electric voltage.

To enable good usability for the medical instrument, it is conceived that the end body in its operating position attached to the connecting body and held by the locking slider will be rotatably mounted to the connecting body. This enables the hand grip to be twisted relative to the sheath tube or relative to an end effector non-rotatably connected with the sheath tube and/or the connecting body.

BRIEF DESCRIPTION OF THE DRAWINGS

Embodiments of the invention are described with reference to the accompanying drawings: Shown are.

DETAILED DESCRIPTION

Figure 1:
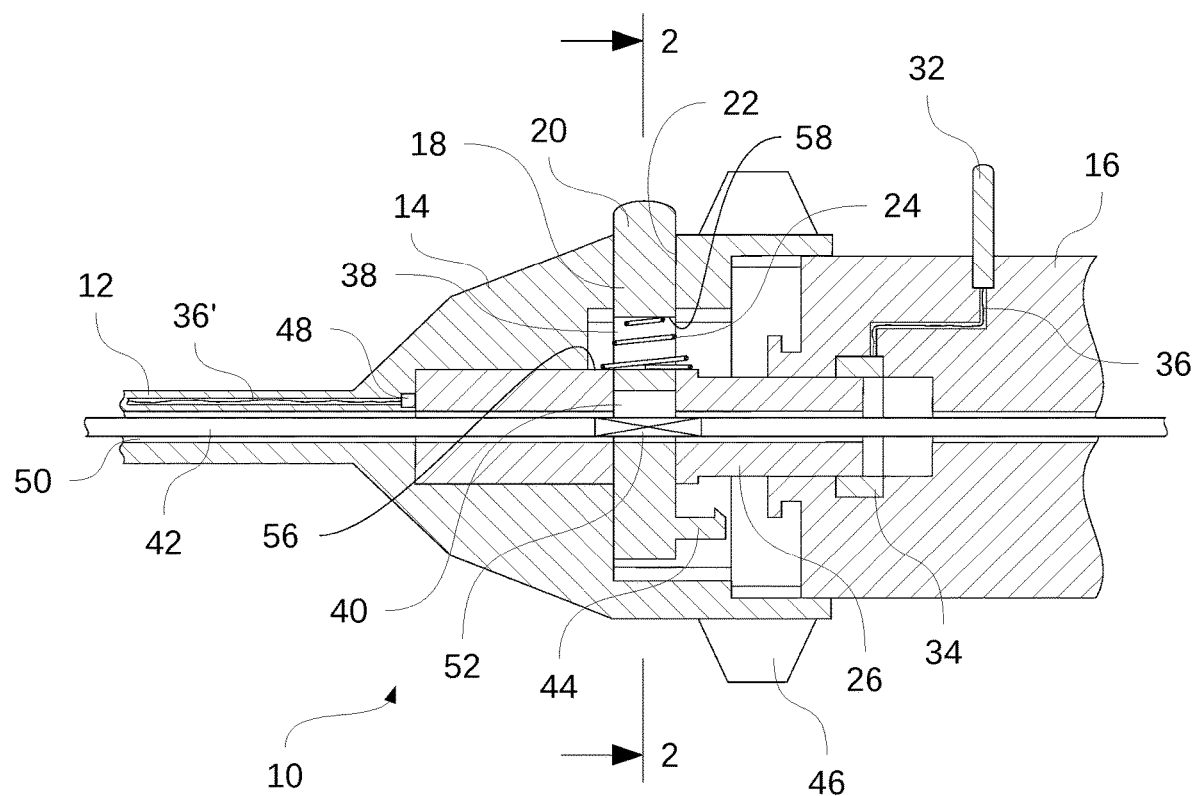
FIG. 1 a cross-sectional view of an instrument according to the invention.

FIG. 1 shows a schematic sectional side view of an instrument 10 according to the invention having an elongated sheath tube 12, to which a connecting body 14 is attached. The connecting body 14 has a transverse shaft 22, within which a locking slider 18 is slidably housed. The locking slider 18, on its end projecting beyond the shaft 22, has an actuating area 20, which can be moved along with the locking slider 18 using, for example, finger pressure against the force applied by a spring 24 in the shaft 22. Attached to the locking slider 18 is a locking hook 44, which is positively lockable with an end body 16 insertable into an axial bore at the proximal end of the connecting body 14. For this purpose, the locking hook 44 engages with a groove in the end body 16. In particular, the groove in the end body 16 can be in the form of an annular groove, so that the end body 16 can be attached to the connecting body 14 such that said end body 14 is rotatable with respect to the sheath tube 12. Preferably, at least portions of the end body are of cylindrical design. The annular groove may—as depicted—be an inward recessed annular gap radial in direction to the longitudinal axis of the end body. The annular groove in the form of the annular gap thus preferably has a gap opening oriented radially outward.

According to the invention, attached to the end body 16 is a hand grip 54 (see FIG. 4), with which the medical instrument 10 can be operated. It is in particular conceivable that an actuating element 42 leading through the sheath tube 12 projects through a bore in the end body 16, said actuating element 42 attachable at its proximal end to the hand grip 54 (see FIG. 4) in such a way that an end effector attached to the actuating element 42 at the distal end of the sheath tube 12 can be actuated using the hand grip 54. This manner of end effector (not shown) may, for example, be forceps, scissors, a knife or the like. The actuating element 42 may be in the form of a push/pull rod. Provided for the passage of the actuating element 42, a common axial channel 50 passes through the medical instrument from the distal end of the sheath tube 12 to the proximal end of the end body 16.

Given the adjustment of the hand grip 54 and the resulting coupled movement of the actuating element 42, for example, two branches of an end effector may be made to actuate in an opening and closing motion. Details of the actuating mechanism and the structural design of the hand grip and/or an end effector arranged at the distal end of the sheath tube 12 can be interpreted from DE 100 64 623 C1, to which explicit reference is hereby made, and/or DE 198 53 305 C1, to which explicit reference is likewise hereby made.

As can be seen in FIG. 1, the spring element 24 in the form of a coil spring is arranged in an interstice 38 in the locking slider 18. The interstice 38 is arranged between the actuation area 20 and the channel 50. The first end of the spring element 24 facing away from the actuation area 20 of the locking slider 18 is supported by a support surface 56 in the area of the channel 50. The second end of the spring element 24 facing toward the actuating area 20 is supported by the contact surface 58 of the locking slider 18. The support surface 56 can, as shown, be provided on a sleeve-like component 26.

An opening 40 is incorporated into the locking slider 18 for the passage of the actuating element 42. The opening 40 is flush with the axial channel 50, which extends through the instrument 10 from the sheath tube 12 to the end body 16. The actuating element 42 in the form of a push/pull rod leads in an axial direction through the sheath tube 12, the connecting body 14 and the end body 16. Within the connecting body 14, the actuating element 42 leads through the sleeve-like component 26.

FIG. 1 shows the medical instrument 10 with an end body 16 detached from the connection body 14. In order to create a coupled connection between the connecting body 14 and the end body 16, the end body 16 in the depicted embodiment is inserted into an axial receptacle bore in the connecting body 14 in such a way that the latching hook 44 of the locking slider 18 engages with an annular ring in the end body 16. As shown, the latching hook 44 may comprise a diagonal sliding surface, which, as the end body 16 is inserted into the connecting body 14, strikes against an area on the edge of the annular ring, forcibly guiding the locking slider 18 against the spring force exerted by the spring element 24 to move into the shaft 22. Upon further movement of the end body 16 into the connecting body 14, the latching hook 44 latches onto the annular ring in the end body 16, positively locking it to the connecting body 14. As shown, it may be provided that the end body 16 be rotatably held to the connecting body 14. For this purpose, the annular groove in the end body 16 is designed as circular ring.

In the end body 16, an electrical junction 32 is provided, via which a signal generator such as a high frequency signal generator, a power source and/or a voltage source can be connected to the medical instrument. Regarding the embodiment of the medical instrument 10 as a bipolar instrument, multiple contacts can be provided at the electrical junction 32, via which electric signals or electric voltages can be transmitted separately from one another to the medical instrument 10. Electric voltage can be transmitted from an electrical junction 32 via an electrical connection 36 to a contact 34, particularly in the form of a sliding contact. Via the contact 34 and via the component 26 within the connecting body 14, the electric voltage can be transmitted to the sheath tube 12. For this purpose, the component 26 can comprise an electrically conductive path or be manufactured from electrically conductive material. It can be provided that, while the end body 16 is attached to or in the coupled position with the connecting body 14, the contact 34 will create an electrically conductive contact with a surface of the component 26. For this purpose, the component 26 may, for example, be manufactured from a metal such as stainless steel. Preferably, the component 26 will be manufactured from an electrically conductive material.

Regarding transmission to the sheath tube 12, the component 26 can transfer the electric voltage to a contact 48 on the sheath tube 12. From the contact 48, the electric signal can be transmitted via an electrically conductive path 36' to the distal end area of the sheath tube 12 and, for example, supplied to an end effector (not shown).

As is evident from FIG. 1, the spring element 24 in the form of a coil spring is supported at its lower end against the electrically conductive component 26 within the connection body 14. Given a component 26 designed using an electrically conductive solid material and the spring element 24 designed likewise using an electrically conductive material such as stainless steel, the spring 24 will likewise be charged with the voltage carried by the component 26.

Figure 3:
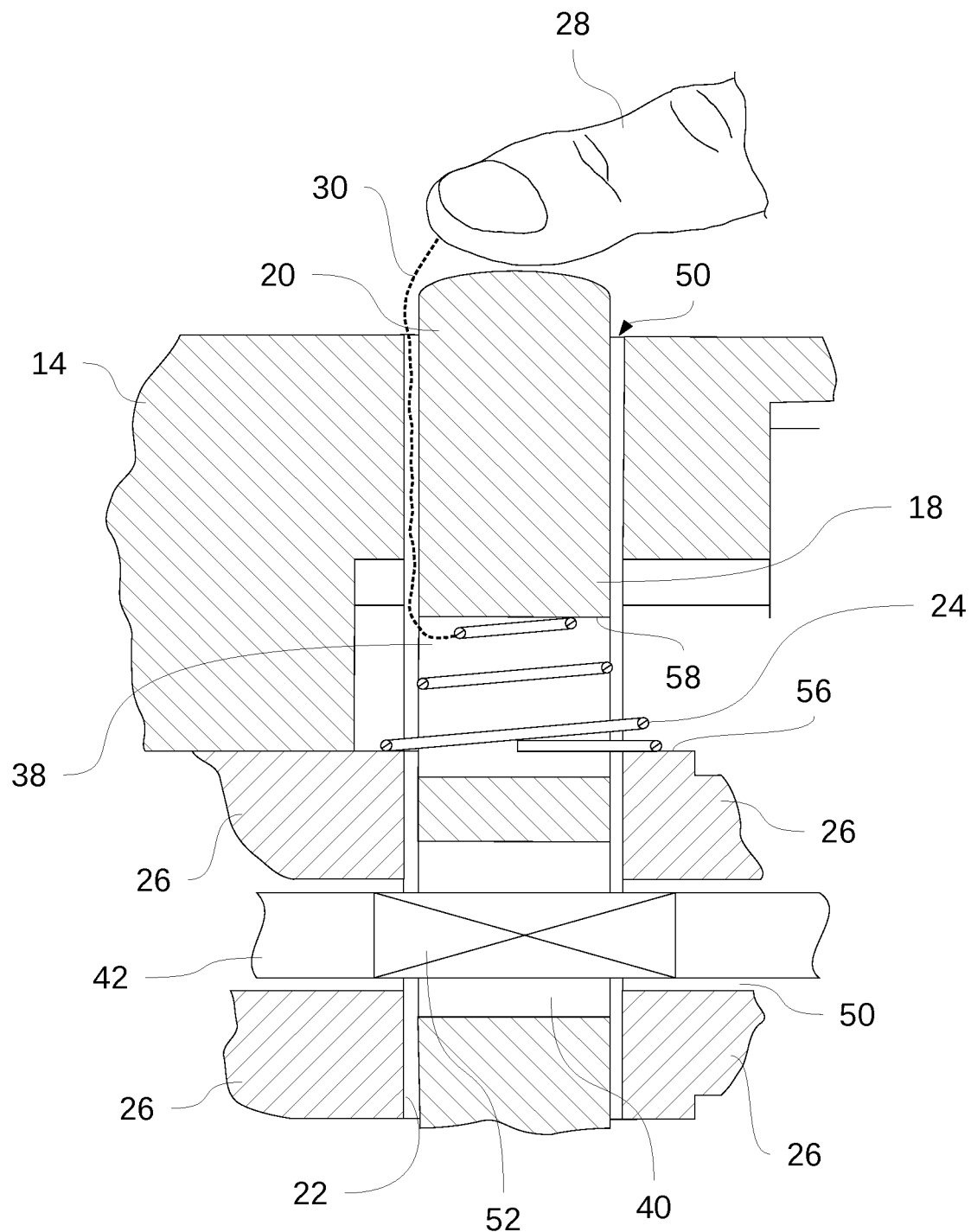
FIG. 3 an enlarged view of a portion of the connecting body with locking slider from FIG. 1, and FIG. 4 a section of the end body from FIG. 1 with a hand grip attached thereto.

As shown in FIG. 3, the hazard may exist of the electric voltage to the coil spring 24 flashing over via a gap 50 to a user, in particular the finger 28 of one using the medical instrument. For purely schematic purposes, a spark gap or leakage current path is shown in FIG. 3 by 30, running between the coil spring 24 and a finger 28. As indicated in FIG. 3, this distance 30 may be extended given that the spring element 24 is in the form of a conical spring. When using a straight coil spring, the distance 30 will be shorter, because a spring 24 of straight coil design will immediately adjoin the circumferential gap 50 around the locking slider 18. Using a spring of conical shape, therefore, allows for the achievement of advantages with regard to construction as well as electrical precautions against flashover. The wide end of a spring of conical shape may, as shown in FIG. 3, project over the edges of an interstice 38 in the locking slider 18 and be supported on a supporting surface 56 of the component 26 with the tapered end fitting against a contact area 58 beneath the actuation area 20 of the locking slider 18. Upon movement of the locking slider 18 within the shaft 22, no portions of the upper end of the spring 24 projecting beyond the opening edge of the interstice 38 and into the shaft 22 can become jammed.

Figure 2:
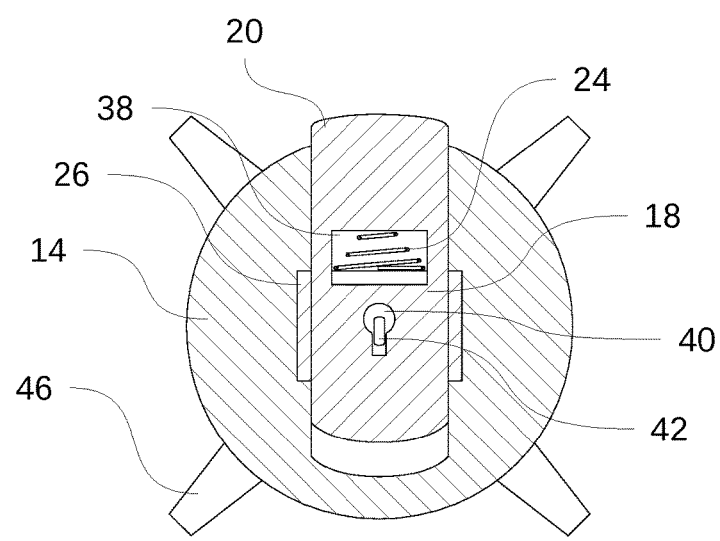
FIG. 2 a schematic view of the locking slider as viewed along the line from 2 to 2 in FIG. 1.

FIG. 2 shows a section of the locking slider 18 and the connecting body 14 as viewed along the line from 2 to 2 in FIG. 1. Using the grip areas 46 projecting radially outward from the connecting body 14, the connecting body 14 can, by a user, be twisted together with the sheath tube 12 with respect to a hand grip mounted on the end body 16 (see FIG. 4). For this purpose, the end body 16 can be rotatably attached to the connection body 14. As shown in FIG. 2, the space beneath the locking slider 18 within the connecting body 14 has a rounded shape. In this way, the wall thickness of the connecting body 14 at the bottom area of the shaft 20 can be thinly formed without increasing the risk of breakage in this area. Minimal wall thicknesses are desirable in order to provide slender and lightweight instruments.

FIG. 3 shows a detail view of the connection body 14 from FIG. 1 in a schematic section view, namely in particular an area of the shaft 22 along which the locking slider 18 runs. In this view, it can be seen that the locking slider 18 has been partially pressed into the shaft 22 via finger pressure by the finger 28 of a user of the medical instrument. In doing so, the spring element 24 in the form of a conical coil spring is slightly compressed. The spring element 24 is supported at its lower end against the supporting surface 56 above the channel 50. At its upper end, the spring element 24 is supported by the contact surface 58 of the locking slider 18. Indicated beneath the spring element 24 is the opening 40, which encompasses an engagement zone 52 of the actuating element 42. The supporting surface 56 is in the form of the surface of the component 26.

In FIG. 3, exaggerated for the purpose of clarity, a gap 50 is evident, which extends between the inner wall of the shaft 22 and the outer wall of the locking slider 18. The dashed line 30 denotes a potential spark gap or leakage current path between the spring element 24 and the finger 28 of a user of the instrument 10. As is clearly shown in FIG. 3, the leakage current path 30 extends through the gap 50 around an edge of the locking slider 18 toward the upper end of the spring element 24 in the form of a conical coil spring.

The use of a conical coil spring increases the electrical safety of the medical instrument 10 in at least in two ways. On the one hand, the leakage current path 30 would be shorter if a straight coil spring were used, as the upper end of the coil spring would end in the immediate area of the gap, and, on the other hand, a direct path within the gap 50 is prevented, because the upper end of the spring element 24 beyond the outer boundaries of the locking slider 18 is engaged inward with respect to the small cross-section of the locking slider 18. The leakage current path 30 is thus guided around an edge of the contact surface 58 of the locking slider 18. This structural design enhances the electrical safety of the medical instrument 10 to the effect that the risk of voltage being transmitted from the spring element 24 to the finger 28 of a user via the gap 50 will be reduced.

Figure 4:
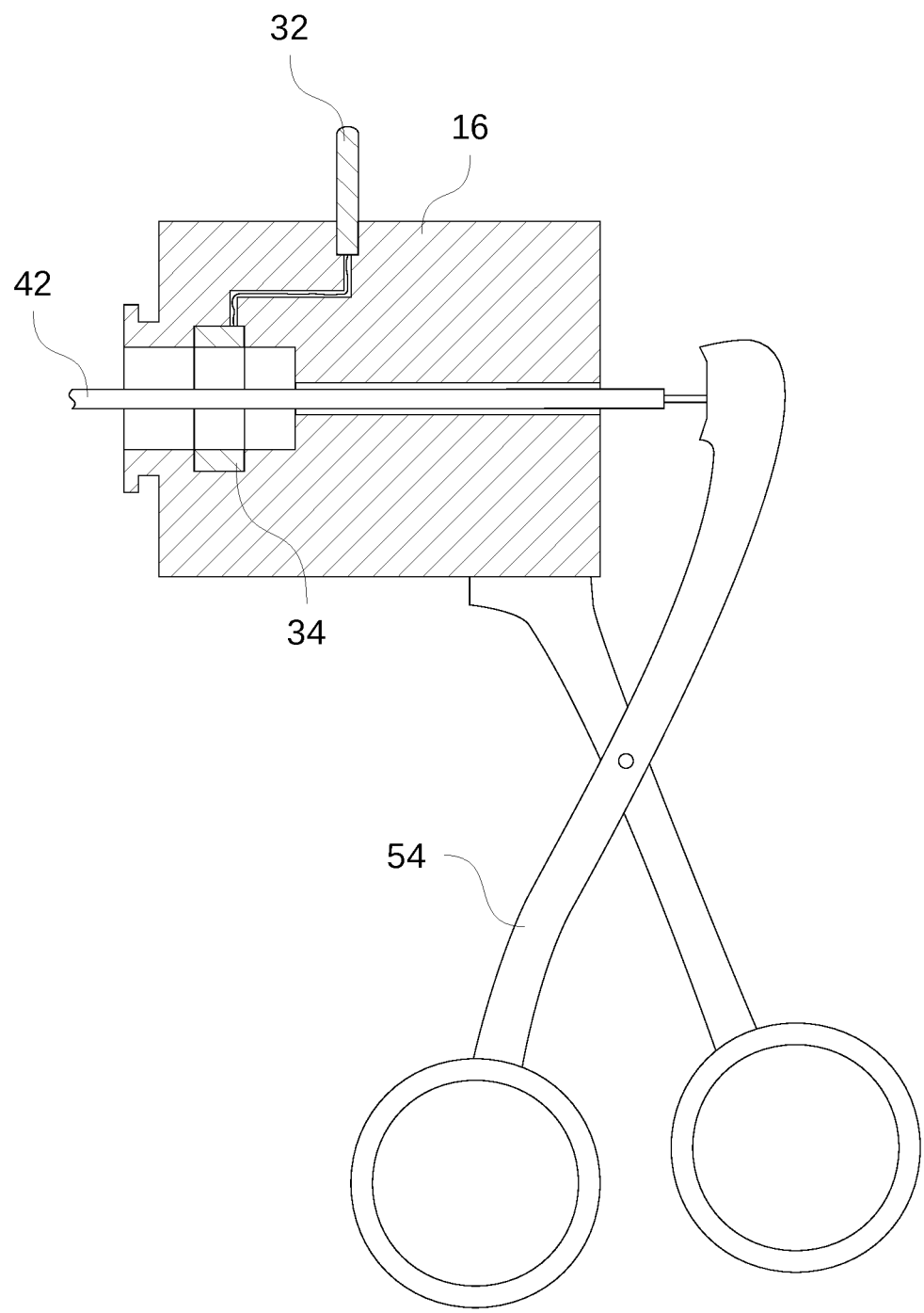

FIG. 4 shows the end body 16 from FIG. 1 with a hand grip 54 attached thereto. As is evident, the hand grip 54 is movably attached at its upper end to the actuating element 42. Upon the actuation of the hand grip 54, a pushing force or pulling force can be translated to the actuating element 42. The hand grip 54 is preferably integrally formed with the end body 16. Alternatively, a detachable connection can be provided between the hand grip 54 and the end body 16.

LIST OF REFERENCE SIGNS

10 medical instrument
12 sheath tube
14 connecting body
16 end body
18 locking slider
20 actuating area
22 shaft
24 spring element
26 component with supporting surface
28 finger
30 leakage current path/spark gap
32 electrical junction
34 electrical contact
36, 36' electrical path
38 interstice in locking slider
40 opening in locking slider
42 actuating element
44 latching hook
46 grip surface
48 electrical contact
50 gap
52 engagement zone
54 hand grip
56 lower support surface for the spring element
58 upper contact surface for the spring element

The invention claimed is:

1. A medical instrument for endoscopic surgery, comprising:
    a power or voltage generator that is configured to generate an electrical current or voltage,
    a sheath tube having a distal and a proximal end and a connecting body arranged at the proximal end area of the sheath tube, whereby the sheath tube and the connecting body are penetrated in the axial direction by a common first channel, through which an elongated actuating element passes,
    an end body connectable to the connecting body having a hand grip attached for operating the medical instrument, and
    a locking slider, which is slidably housed in a second channel oriented at an angle to the first channel within the connecting body, whereby an actuation area of the locking slider projects from the connecting body and can be actuated to locked and free positions using finger pressure, such that the end body coupled to the connecting body is positively locked to the connecting body in the locked position, and the end body in the free position can be detached from the connecting body, and whereby the locking slider is held in the locked position by the tension of a spring element, wherein
    the spring element is arranged in the second channel between the actuation area and the first channel, and
    the spring element is a tapered coil spring that is configured to provide a longer leakage current path from the power or voltage generator.

2. The medical instrument according to claim 1, wherein at a first end along the direction of spring compression facing away from the actuating area the spring element is supported by a support surface situated in the area of the first channel, and along the direction of spring compression facing toward the actuating area the spring element is supported by a contact surface on the locking slider.

3. The medical instrument according to claim 2, wherein the cross-sectional area of the spring element tapers from the first end to the second end.

4. The medical instrument according to claim 2, wherein at least in the section provided for the spring element between the actuating area and the first channel, the locking slider has a cross-section which is narrower in a first direction and wider in a second direction than a cross-section at the first end of the spring element.

5. The medical instrument according to claim 1, wherein the spring element is arranged in an interstice in the locking slider.

6. The medical instrument according to claim 1, wherein a junction is arranged on the end body for coupling an electric voltage to the sheath tube and/or to an actuating element leading through the first channel.

7. The medical instrument according to claim 1, wherein the locking slider comprises an opening for letting through the actuating element.

8. The medical instrument according to claim 7, wherein the opening comprises a passage zone and a holding zone, whereby, in the free position, the locking slider allows a proximal section of the actuating element leading through the first channel to freely pass through the passage zone, and, in the locked position, an engagement zone of the actuating element encompasses and positively locks free of rotation with the holding zone.

9. The medical instrument according to claim 1, wherein the end body while in its operational configuration connected to the connecting body is rotatably mounted to said connecting body.

* * * * *